C807A XR 4,261,975

[redacted] [redacted] [redacted] ]

[11] 4,261,975

[45] Apr. 14, 1981

Fullerton et al.

[54] VIRAL LIPOSOME PARTICLE

[75] Inventors: W. Wardle Fullerton, King of Prussia; Bohdan Wolanski, Norristown, both of Pa.

[73] Assignee: Merck & Co., Inc., Rahway, N.J.

[21] Appl. No.: 77,249

[22] Filed: Sep. 19, 1979

Related U.S. Application Data

[63] Continuation-in-part of Ser. No. 958,778, Nov. 8, 1978, Pat. No. 4,201,767.

[51] Int. Cl.$^3$ .................... A61K 39/12; A61K 39/145

[52] U.S. Cl. .................................................. 424/89

[58] Field of Search ........................ 424/36, 39, 88-93

[56] References Cited

U.S. PATENT DOCUMENTS

| | | | |
|---|---|---|---|
| 4,016,100 | 4/1977 | Suzuki | 424/36 |
| 4,053,585 | 10/1977 | Allison et al. | 424/92 |
| 4,078,052 | 3/1978 | Papahadjopoulos | 424/36 |
| 4,089,801 | 5/1978 | Schneider | 424/36 |
| 4,117,113 | 9/1978 | Allison et al. | 424/89 |
| 4,145,410 | 3/1979 | Sears | 424/36 |
| 4,148,876 | 4/1979 | Almeida et al. | 424/89 |
| 4,186,183 | 1/1980 | Steck et al. | 424/38 |

OTHER PUBLICATIONS

Chem. Abstracts 88:1961t, (1978) 89:1994b:157972d:100739d (1978), Grupe et al., Interaction of Homologows Quaternary . . . (Lipid Membranes (I, II, III, IV).

*Primary Examiner*—Shep K. Rose

*Attorney, Agent, or Firm*—Donald J. Perrella; Julian S. Levitt; Rudolph J. Anderson

[57] ABSTRACT

The outer membrane of influenza virus is attached to a liposome by two different techniques. In addition, one of the techniques allows the entrapment of intact virus, usually one virus per liposome. The techniques can be performed with either influenza virus A or B.

10 Claims, No Drawings

VIRAL LIPOSOME PARTICLE

RELATED APPLICATION

This application is a continuation-in-part of application Ser. No. 958,778 filed Nov. 8, 1978, now U.S. Pat. No. 4,201,767.

BACKGROUND OF THE INVENTION

By attempting to purify influenza virus as much as possible, its undesirable side effects have been reduced but at the same time its antigenic effect also has been reduced.

OBJECTS OF THE INVENTION

It is an object of the present invention to increase the antigenicity of an influenza virus preparation. Another object is to reduce the toxicity of the influenza virus. Another object is to provide a simpler and more economical process for purifying influenza virus and isolating antigenic subunits. A further object is to provide a particle wherein the outer membrane of influenza virus is attached to a liposome. Still another object is to provide a liposome having an intact whole influenza virus inside. Yet another object is to provide a method for preparing such particles. These and other objects of the present invention will be apparent from the following description.

SUMMARY OF THE INVENTION

The outer membrane of influenza virus A or B is attached to a liposome by (1) reaction with a mixture of a natural or synthetic phosphocholine-containing lipid and a positively charged amino-containing surfactant or (2) reaction with a positively charged amino-containing surfactant followed by reaction with a natural or synthetic phosphochloine-containing lipid. In addition by the first technique some virus is entrapped inside some of the liposomes, usually one virus per liposome.

DETAILED DSECRIPTION

The present invention relates to influenza vaccine and, more particularly, to a subunit influenza vaccine wherein the outer membrane of the influenza virus is attached to a liposome. One technique, in addition, allows whole virus to be entrapped inside the liposome. A liposome is a continuous lipid surface, either unilamellar or multilamellar, enclosing a three-dimensional space.

It has been found according to the present invention that the outer membrane of the influenza virus can be removed from the rest of the influenza virus particle and reattached to the outer surface of a liposome containing phospholipid and an amino-containing surfactant which has a positive charge. The viral spikes of the influenza virus remain intact in this process. The resulting particle, a liposome having fused thereto the outer membrane of the influenza virus with intact spikes, has been named a spikoliposome.

The liposome is prepared from either a natural or synthetic phosphocholine-containing lipid having one fatty acid chain of from 12 to 20 carbon atoms and one fatty acid chain of at least 8 carbon atoms. In general, synthetic lipids are preferred as they have fewer impurities. A preferred synthetic lipid is a phosphatidylcholine containing two fatty acid side chains from 12 to 20 carbon atoms. Some suitable synthetic lipids are, for example:

dimyristoylphosphatidylcholine,
dioleoylphosphatidylcholine,
dipalmitoylphosphatidycholine, and
distearoylphosphatidylcholine, while some suitable natural lipids are, for example:

phosphatidylcholine, and
sphingomyelin.

The positively charged amino-containing surfactant may be a fatty acid amine of from 12 to 20 carbon atoms such as, for example, laurylamine, cetylamine and stearylamine, or a positively charged quaternary ammonium salt of an amino-containing surfactant of the formulas

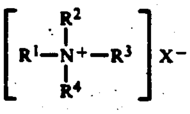
or
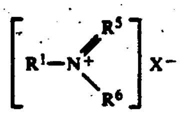

wherein $R^1$ is a straight or branched chain alkyl radical of from 12 to 20 carbon atoms, $R^2$ and $R^3$ may be the same or different and are alkyl of from 1 to 3 carbon atoms, and $R^4$ is benzyl, $R^5$ and $R^6$ together are a 5-membered or 6-membered heterocyclic radical such as for example, pyridine or pyrrole, and X is a halide ion, preferably chloride or bromide. Some examples of suitable positively charged aminocontaining surfactants are cetyl benzyldimethyl ammonium chloride,
N-hexadecylpyridinium chloride,
hexadecyltrimethyl ammonium bromide, and
cetyltrimethyl ammonium bromide.

In preparing the spikoliposome virus particle of the present invention, the positively charged amino-containing surfactant and the phospholipid are dried together. The influenza virus in aqueous medium (water or low molarity buffer, pH 6.8–7.4), is then added under liposome forming conditions, such as agitation, e.g., bath sonication for from about 2 to about 8 minutes, to form positively charged liposomes to which the outer membrane of the virus is fused. The resulting particle is a spikoliposome, that is, a liposome having fused thereto the outer membrane of influenza virus with the spikes intact. In the same preparation there also exists liposomes having no spikes fused thereto but which contain usually one entrapped intact influenza virus per liposome.

In a second technique the virus is reacted directly with the positively charged surfactant. This, as an aqueous (water only) suspension, is then added to the dry phospholipid and the preparation agitated, e.g., by bath sonication for from about 2 to about 8 minutes, to form positively charged liposomes to which the outer membrane of the virus is fused. The resulting particle is a spiloliposome, that is, a liposome having fused thereto the outer membrane of influenza virus with the spikes intact.

The preparation containing both types of particles may be administered as an influenza vaccine but, if desired, the particles may be separated by centrifugation and column chromatography, and adminstered individually as an influenza vaccine.

The following examples illustrate the present invention without, however, limiting the same thereto.

EXAMPLE 1

Dioleoylphosphatidylcholine (20 mg in 0.8 ml chloroform) and stearylamine (3 mg dry powder dissolved in 1-2 ml dry chloroform) are mixed together for 3-5 minutes in a 25 ml round bottom or pear-shaped flask and then dried down in vacuo at 37° C. Immediately after drying, dry nitrogen gas is blown into the flask and 3.5 ml of the influenza virus preparation is added slowly. The virus preparation previously has been dialyzed aseptically in ¼" cellulose dialysis tubing for 18 hours at 2°-4° C. against three charges of 1 liter each of 0.063 M sodium phosphate buffer (pH 7.0) and contains approximately 560 CCA/ml. Nitrogen gas is continuously bubbled through the solution which is placed in the center of a small (13.5 cm×13.5 cm) ultrasonic cleaner bath (Cole-Parmer) filled 6 cm-8 cm deep with water which contains 1 ml of Triton X-100 as detergent. The cleaner bath operates at 50-55 KHz and is maintained at 20°-22° C. by addition of ice. The solution is sonicated, with occasional swirling of the contents, for 7 minutes. After sonication the contents of the flask are transferred to a 6 ml serum bottle and capped with a rubber stopper. The sonicated material is stored at 2°-4° C. The preparation is stable for at least five months.

EXAMPLE 2

Stearylamine (3 mg) plus ethanol (0.4 ml) are heated to 55°-60° C. for 1-2 minutes until the stearylamine is completely soluble. Then deionized water (2.6 ml) which has been heated to 55°-60° C. is slowly added with swirling. At this stage the solution may be opalescent, but there is no precipitate. Pure dry nitrogen gas is bubbled through the solution for 10 minutes until the solution is cooled to 28°-34° C. Then 0.9 ml of influenza virus which has been dialyzed as in Example 1 and containing approximately 2200 CCA/ml is slowly added at room temperature and nitrogen gas bubbled through for a further 4 minutes. No obvious precipitate is present. Next, the virus-stearylamine preparation is slowly added to a dried down preparation of dioleoylphosphatidylcholine (20 mg) in a 25 ml round bottom or pear-shaped glass flask. While continuously bubbling nitrogen gas through, the preparation is sonicated for 7 minutes in a Cole-Parmer ultrasonic cleaner bath at 50-55 KHz. The temperature of the cleaner bath is maintained at 20°-22° C. by the addition of ice. During sonication the contents of the flask are occasionally swirled. After sonication the contents of the flask are transferred to a 6 ml serum bottle, capped with a rubber stopper, and stored at 2°-4° C. where the preparation is stable for at least three months. The final concentration of virus is approximately 560 CCA/ml.

EXAMPLE 3

The spikoliposome preparation of Example 2 is compared with aqueous influenza vaccine, dialyzed aqueous influenza vaccine, each containing New Jersey type A influenza virus and a vaccine consisting of the spikoliposome preparation of Example 2 without virus. Each is administered to a group of guinea pigs, 8 animals per test, at a virus concentration of 100 CCA units per dose, and the geometric mean hemagglutination-inhibition titer is calculated on day of injection as well as 21 and 42 days following injection. The following results are obtained.

| | | Geometric Mean HI antibody titer at day | | |
|---|---|---|---|---|
| Test | Vaccine | 0 | 21 | 42 |
| 1 | PBS (control) | <10 | <10 | <10 |
| 2 | Liposomes, no virus | <10 | <10 | <10 |
| 3 | Aqueous vaccine | <10 | 1:52 | 1:17 |
| 4 | Dialyzed aqueous vaccine | <10 | 1:40 | 1:12 |
| 5 | Spikoliposome preparation of Example 2 | <10 | 1:85 | 1:56 |

EXAMPLE 4

Spikoliposome preparations prepared according to Example 2 using type A Victoria and type B Hong Kong influenza virus and various lipids are administered to a group of 8 mice and the arithmetic means hemagglutination inhibition titer calculated 42 days following injection with the following results. An aqueous influenza vaccine without spikoliposomes is used as control.

| Lipid | Titer of whole formalin killed A/Victoria influenza virus at 50 CCA units/dose | Titer of whole formalin killed B/Hong Kong influenza virus at 50 CCA units/dose |
|---|---|---|
| None (Control) | 20 | 20 |
| Dioleoylphosphatidylcholine | 40 | 80 |
| Dipalmitoylphosphatidylcholine | 40 | 80 |
| Sphingomyelin | 80 | 80 |

EXAMPLE 5

Spikoliposome preparations produced in accordance with Examples 1 and 2 using A/Victoria and B/Hong Kong influenza virus and whole formalin killed aqueous influenza vaccines made with the same two viruses but without spikoliposomes are administered to a group of 8 mice and the geometric mean hemagglutination inhibition antibody titer is determined 30 days following injection. The following results are obtained.

| Spikoliposome of Example | Influenza Virus | CCA units/dose 50 | 5 |
|---|---|---|---|
| 1 | A/Victoria | 1:62 | 1:28 |
| 1 | B/Hong Kong | 1:40 | 1:11 |
| 2 | A/Victoria | 1:37 | 1:11 |
| 2 | B/Hong Kong | 1:44 | 1:19 |
| No spikoliposome | Whole formalin killed A/Victoria | 126 | 1:5 |
| No spikoliposome | Whole formalin killed B/Hong Kong | 1:12 | 1:7 |

What is claimed is:

1. A spikoliposome particle comprising a liposome having attached to its outer surface the intact outer membrane layer of influenza virus having attached spikes, the outer membrane attached by having been reacted with both a positively charged quaternary ammonium salt of an amino-containing surfactant of the formulas

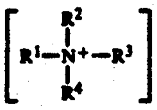 or 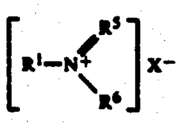

wherein $R^1$ is a straight or branched chain alkyl radical of from 12 to 20 carbon atoms, $R^2$ and $R^3$ may be the same or different and are alkyl of from 1 to 3 carbon atoms, and $R^4$ is benzyl, $R^5$ and $R^6$ together are a 5-membered or 6-membered heterocyclic radical, and X is a halide ion, and a phospholipid.

2. A spikoliposome according to claim 1 wherein the virus is influenza type A or influenza type B.

3. A liposome according to claim 1 wherein the virus is influenza type A or influenza type B.

4. A composition containing a spikoliposome particle according to claim 1.

5. A spikoliposome according to claim 1 wherein the liposome is formed from a phosphatidylcholine-containing lipid.

6. A method of preparing a spikoliposome particle according to claim 1 comprising the step of agitating under liposome forming conditions an aqueous medium containing whole influenza virus, a positively charged amino-containing surfactant and a phosphatidylcholine-containing lipid.

7. A method of preparing a spikoliposome particle according to claim 1 comprising the step of agitaging under liposome forming conditions an aqueous medium containing a phosphatidylcholine-containing lipid and an adduct formed by reacting whole influenza virus with a positively charged amino-containing surfactant.

8. A method of preparing a composition containing a spikoliposome particle according to claim 1 comprises the step of agitating under liposome forming conditions an aqueous medium containing whole influenza virus, a positively charged amino-containing surfactant and a phosphatidylcholine-containing lipid.

9. A method according to claim 8 wherein the liposome forming conditions comprise bath sonication.

10. A method according to claim 9 wherein the liposome forming conditions comprise bath sonication.

* * * * *